(12) United States Patent
Zeller et al.

(10) Patent No.: US 8,487,016 B2
(45) Date of Patent: Jul. 16, 2013

(54) DENTAL IMPRESSION MATERIAL CONTAINING RHEOLOGICAL MODIFIERS AND PROCESS OF PRODUCTION

(75) Inventors: Sebastian Zeller, Cologne (DE); Thomas Klettke, Diessen (DE); Peter Bissinger, Diessen (DE)

(73) Assignee: 3M Innovative Properties Company, St. Paul, MN (US)

( * ) Notice: Subject to any disclaimer, the term of this patent is extended or adjusted under 35 U.S.C. 154(b) by 223 days.

(21) Appl. No.: 12/809,187

(22) PCT Filed: Dec. 17, 2008

(86) PCT No.: PCT/US2008/087113
§ 371 (c)(1),
(2), (4) Date: Jun. 18, 2010

(87) PCT Pub. No.: WO2009/085799
PCT Pub. Date: Jul. 9, 2009

(65) Prior Publication Data
US 2011/0257290 A1    Oct. 20, 2011

(30) Foreign Application Priority Data

Dec. 20, 2007  (EP) .................................. 07150196

(51) Int. Cl.
*A61K 6/10* (2006.01)
(52) U.S. Cl.
USPC .......................................... 523/109; 523/433
(58) Field of Classification Search
USPC .................................... 523/109, 433
See application file for complete search history.

(56) References Cited

U.S. PATENT DOCUMENTS

| | | | | |
|---|---|---|---|---|
| 1,995,963 A * | 3/1935 | Croce | | 106/661 |
| 2,359,512 A * | 10/1944 | Dickson al. | | 106/38.35 |
| 3,440,207 A * | 4/1969 | Wick et al. | | 523/212 |
| 3,453,242 A * | 7/1969 | Zahler et al. | | 528/322 |
| 4,167,618 A | 9/1979 | Schmitt | | |
| 4,182,829 A * | 1/1980 | Walkowiak et al. | | 528/75 |
| 4,198,243 A * | 4/1980 | Tanaka | | 106/31.03 |
| 4,265,669 A * | 5/1981 | Starling et al. | | 501/153 |
| 4,493,911 A * | 1/1985 | Schmitt et al. | | 523/109 |
| 4,532,268 A | 7/1985 | Jochum | | |
| 4,585,417 A * | 4/1986 | Sozio et al. | | 433/202.1 |
| 4,835,203 A * | 5/1989 | Sieverding | | 524/227 |
| 4,867,790 A | 9/1989 | Jochum | | |
| 5,249,862 A | 10/1993 | Herold | | |
| 5,286,105 A | 2/1994 | Herold | | |
| 5,332,122 A | 7/1994 | Herold | | |
| 5,464,131 A | 11/1995 | Keller | | |
| 5,569,691 A * | 10/1996 | Guggenberger et al. | | 524/261 |
| 5,924,600 A | 7/1999 | Keller | | |
| 6,040,354 A | 3/2000 | Hübner | | |
| 6,127,449 A | 10/2000 | Bissinger | | |
| 6,135,631 A | 10/2000 | Keller | | |
| 6,244,740 B1 | 6/2001 | Wagner | | |
| 6,395,801 B1 | 5/2002 | Bissinger | | |
| 6,762,242 B1 * | 7/2004 | Torto et al. | | 524/588 |
| 6,894,144 B1 | 5/2005 | Zech | | |
| 7,022,763 B2 * | 4/2006 | Matsugi et al. | | 525/63 |
| 7,276,545 B2 | 10/2007 | Eckhardt | | |
| 7,812,065 B2 * | 10/2010 | Bublewitz et al. | | 523/109 |
| 2003/0153726 A1 | 8/2003 | Eckhardt | | |
| 2004/0085854 A1 | 5/2004 | Pauser | | |
| 2005/0250871 A1 * | 11/2005 | Bublewitz et al. | | 523/109 |
| 2006/0047063 A1 | 3/2006 | Schaub | | |
| 2006/0204452 A1 * | 9/2006 | Velamakanni et al. | | 424/49 |
| 2006/0205838 A1 * | 9/2006 | Velamakanni et al. | | 523/115 |
| 2007/0004821 A1 * | 1/2007 | Bublewitz et al. | | 523/109 |
| 2007/0173557 A1 | 7/2007 | Bublewitz | | |
| 2008/0319100 A1 * | 12/2008 | Bublewitz et al. | | 523/109 |

FOREIGN PATENT DOCUMENTS

| | | |
|---|---|---|
| DE | 858170 | 7/1949 |
| DE | 914325 | 7/1949 |
| DE | 1745810 | 1/1970 |
| DE | 3245052 | 6/1984 |
| DE | 4306997 | 9/1994 |
| DE | 4321257 | 8/1996 |
| DE | 19505896 | 8/1996 |
| DE | 19517962 | 11/1996 |
| DE | 19711514 | 9/1999 |
| DE | 19942459 A1 | 3/2001 |
| DE | 10018918 | 11/2001 |
| EP | 0232733 | 8/1987 |
| EP | 0279238 | 8/1988 |
| EP | 0730913 | 9/1996 |
| EP | 0811039 | 12/1997 |
| EP | 0863088 | 9/1998 |
| EP | 1563823 | 8/2005 |

(Continued)

OTHER PUBLICATIONS

Synthesis of Oleoylethanolamide Using Lipase, Wang et al. Agricultural and Food Chemistry.*
Acrawax C Technical Data Sheet, Mar. 3, 2003.*
Glycolube VL Technal Data Sheet, Nov. 16, 2005.*
N,N Ethylene bis (stearamide) Properties, 2008.*
Schott, "Hydrophile-Lipophile Balance and Cloud Points of Nonionic Surfactants", J. Pharm. Science, Dec. 1969, vol. 58, No. 12, pp. 1443-1449.
Ullmann's Encyklopädie der technischen Chemie, 4th Edition, Book 24, Germany, Wachse bis Zündhölzer, 1983, "Definition of Wax", p. 3.

(Continued)

*Primary Examiner* — James J Seidleck
*Assistant Examiner* — Peter A Salamon
(74) *Attorney, Agent, or Firm* — Stephen L. Crooks; Pamela L. Stewart

(57) ABSTRACT

The invention relates to a dental impression material containing a rheological modifier. The rheological modifier is in particular useful for adjusting shear-thinning properties of non-water based dental impression materials, especially of precision impression materials. It further relates to a method for producing a dental impression material.

12 Claims, No Drawings

FOREIGN PATENT DOCUMENTS

| | | |
|---|---|---|
| EP | 1820815 | 8/2007 |
| EP | 1913090 | 4/2008 |
| WO | WO 96/26246 | 8/1996 |
| WO | WO 02/102877 | 12/2002 |
| WO | WO 2004/098542 | 11/2004 |
| WO | WO 2007/016295 | 2/2007 |
| WO | WO 2007/024564 | 3/2007 |
| WO | WO 2007024564 A1 * | 3/2007 |
| WO | WO 2007080071 A2 * | 7/2007 |

OTHER PUBLICATIONS

Written Opinion of International Application No. PCT/US2008/087113, 7 pages.

Search Report of International Application No. PCT/US2008/087113, 4 pages.

Sagnella, Sharon M., et al.; "Ordered Nanostructured Amphiphile Self-Assembly Materials from Endogenous Nonionic Unsaturated Monoethanolamide Lipids in Water", LANGMUIR, vol. 26, No. 5, Nov. 20, 2009, pp. 3084-3094, DOI: 10.1 02111a903005q.

* cited by examiner

DENTAL IMPRESSION MATERIAL CONTAINING RHEOLOGICAL MODIFIERS AND PROCESS OF PRODUCTION

CROSS REFERENCE TO RELATED APPLICATIONS

This application is a national stage filing under 35 U.S.C. 371 of PCT/US2008/087113, filed Dec. 17, 2008, which claims priority to European Application No. 07150196.9, filed Dec. 20, 2007, the disclosure of which is incorporated by reference in its/their entirety herein.

FIELD OF THE INVENTION

The present invention relates to dental impression materials and in particular to non-water based dental precision impression materials which can be used to record the oral situation of a patient. The resulting impression captures the negative oral situation. After casting this impression a positive model of the oral situation is recovered.

BACKGROUND

Different types of chemistry can be employed to formulate impression materials. Mostly used are polyether impression materials cured by a cationic ring-opening polymerization of aziridines (e.g. Impregum™, 3M ESPE), polysiloxanes cured via a hydrosylation reaction (e.g. Aquasil™, Dentsply) polysiloxanes cured via a condensation mechanism (e.g. Xantropren™, Heraeus Kulzer), mixtures of polyethers and siloxanes cured via a hydrosylation mechanism (e.g. Senn™, GC) or polyethers cured via a condensation mechanism (e.g. P2™, Heraeus Kulzer).

Dental impression materials are typically reactive systems that cure in the patient's mouth in order to record the oral situation. Mostly dental impression materials are delivered as two pastes, a base paste and a catalyst paste, which are mixed together prior to their application. With the help of a dental tray and a syringe-type device for syringing material around the prepared tooth or teeth the mixed paste is delivered in the patient's mouth. Usually the cured material can be removed between one and six minutes after tray seating. The finished impression is used either to make a provisional restoration or it is to be casted to form a casting model and make the final restoration in the dental laboratory.

The base paste and the catalyst paste of the dental impression materials as well as their mixture in the state before the curing should have shear-thinning properties. Shear-thinning is the feature of a fluid to show a decreasing viscosity at increasing shearing force. Thus, shear thinning ensures a low viscosity at a high shear rate and a high viscosity at a low shear rate. This behaviour can sometimes be desirable. In a first aspect it may simplify the mixing process of the base paste with the catalyst paste. In a second aspect the risk of dropping under gravity of the mixed impression material is reduced (e.g. dropping of the material from the upper jaw). Further, it should nicely flow to gingiva, into small gaps and around teeth when syringed or when the tray is seated. Also under the compression of a delivery device like a hand dispenser (e.g. supplied by SulzerMixpac) or an electronic mixing device (e.g. Pentamix™, 3M ESPE) the material (base paste, catalyst paste and mixture of the pastes) should flow nicely. Using the terminology of rheometry the paste can be characterized by its viscosity at different shear rates. At low shear rates a high viscosity is desired whereas at high shear rates a low viscosity is desirable.

In the prior art, to achieve these shear-thinning properties for dental impression materials two major classes of rheology modifiers are used, highly dispersed silica and fats.

For instance, DE 43 21 257 A1 suggests the use of pyrogenic and/or precipitated silica with a BET surface of 25 to 600 $m^2/g$ to improve polymerizable polyether materials.

In DE 197 11 514 A1 (also published as U.S. Pat. No. 6,127,449) teaches to use 5 to 20 wt.-% of a triacylglyceride of a non-animal source as rheology modifier for impression material based on polymerizable polyether material.

DE 195 17 962 A1 (also published as U.S. Pat. No. 6,040, 354) discloses a material based on polysiloxanes containing at least one wax except paraffin or microwax. The method to produce this material includes heating the mixture above the melting point of the wax, to emulsify the mixture and to cool the emulsion rapidly. Only after storing at room temperature for about 12 hours the fillers and rheological modifiers can be incorporated into the material with a separate kneading step.

EP 1 563 823 A2 (also published as US 2005/250871) discloses dental material based on alkoxysilylfunctionalized polyethers with a catalyst. As thixotropic agents different substances can be added.

U.S. Pat. No. 5,569,691 relates to a rubber-elastic composition comprising a vulcanizable polyether material and at least one hydrophilic nature imparting agent. In Example 4 (Comparative Example) a composition is described containing besides an aziridino polyether a certain amount of a substance designated Telamide™. The properties of this substance have been tested in the experimental section of the present invention.

US 2006/47063 describes compositions containing at least one silane-terminated polyether derivative. As fillers are used organic fillers like hydrogenated castor oil or castor oil derivatives, polyamides, polyesters, paraffins, waxes and fats. The compositions mandatory comprise water.

A disadvantage of using waxes of the state of the art as rheological modifiers is sometimes the complicated production process which involves a melting step in a vessel followed by a shock-cooling step using a shock cooling roller in which the liquid components of the paste and the molten triglyceride are subjected. Finally, after storing the material for some hours at about room temperature, a further kneading step in a kneader is necessary to incorporate the fillers and rheological modifiers.

For many materials of the state of the art, highly dispersed silica or more general highly dispersed oxides are used. These compounds optionally may be surface treated.

Highly dispersed silica is relatively cheep. Also a wide variety of materials differing in surface area and surface treatment is available. Examples are Aerosil™ (Degussa) or HDKH™ (Wacker). In general the highly dispersed silica might be reacted with hydrophilic, hydrophobic, reactive or unreactive substances in order to achieve the desired surface treatment.

A disadvantage of using highly dispersed silica types in dental formulations together with the reactive monomers or pre-polymers that form dental impression materials is the relatively low shelf life of the components of the impression material prior mixing. This in particular refers to the base paste. Si—OH groups which are located at the surface are highly reactive. It is known to the specialist that it is impossible to react all Si—OH groups at the surface of highly dispersed silica. Remaining Si—OH groups are responsible for the compromised shelf life of the reactive systems.

For example, Si—OH groups are incompatible with aziridines, the reactive group of e.g. aziridino-polyethers that build one group of reactive monomers or pre-polymers, since traces of acidic components cause early polymerization.

In conjunction with residual water which is always present in fillers and in polyethers e.g. in monomers, pre-polymers or surfactants, Si—OH groups are also incompatible with Si—H functions that form the reactive group used in the impression materials cured via hydroxylation. The loss of Si—H functions is observed which results in reduced speed of cure, reduced cross link density accompanied by lower mechanical values and hydrogen release which might be an issue for materials delivered in foil bags.

In conjunction with residual water Si—OH groups are also incompatible with $Si(OR)_x$ [x=1, 2, 3; R=alkyl preferably Me or Et] functions that form the reactive group in the materials cured via condensation reaction. The systems tend to the loss of reactive functions and to pre-polymerization.

SUMMARY OF THE INVENTION

Therefore it would be desirable to provide a polymerizable dental material with an improved shear thinning behaviour.

It would further be desirable to find a process for manufacturing polymerizable dental materials with good shear-thinning behaviour with a reduced number of production steps.

Thus, in one embodiment the invention is directed to a polymerizable dental impression material comprising at least one amide wax and/or at least one modified amide wax wherein the amide wax and/or the modified amide wax is a compound or a mixture of compounds having wax properties and the compound or at least one compound of the mixture has at least one amide group and wherein the amide wax and/or the modified amide wax has a melting temperature or an area of melting temperatures of above about 60° C.

Another embodiment of the invention relates to a polymerizable dental impression material comprising
(a) a polyether compound containing N-alkylaziridine-groups,
(b) a catalyst compound,
(c) filler,
(d) optionally additives selected from the group consisting of dyes, pigments, flavourings, stabilizers, retarders, accelerators, other auxiliary compounds and combinations thereof, and
(e) at least one amide wax and/or at least one modified amide wax wherein the amide wax and/or the modified amide wax is a compound or a mixture of compounds having wax properties and the compound or at least one compound of the mixture has an amide group and wherein the amide wax and/or the modified amide wax has a melting temperature or an area of melting temperatures of above 60° C.

Yet another embodiment of the invention features a process of producing a polymerizable dental impression material, comprising the steps of:
(a) heating one ore more of the liquid ingredients of a dental impression material to a temperature of about 40 to about 140° C. or of about 60 to about 120° C.,
(b) adding at least one amide wax and/or at least one modified amide wax to the heated liquid mixture wherein the amide wax and/or the modified amide wax has a melting temperature or an area of melting temperatures above the temperature to which the ingredients of step (a) are heated,
(c) incorporating the amide wax(es) and/or the modified amide wax(es) to the mixture by dissolving it with a dissolver at a temperature which is below the melting temperature or below the area of melting temperatures of the added amide wax(es) and/or the modified amide wax(es) until the mixture becomes clear,
(d) optionally adding additives,
(e) cooling the mixture down to room temperature (23° C.), and
(f) optionally adding flavourants.

The invention also relates to a non-water based dental impression material which can be casted with gypsum without significant loss in accuracy over a period of days.

DEFINITIONS

Within the description of the invention, the following terms are defined as follows:

The term "compound" is a chemical substance which has a particular molecular identity or is made of a mixture of such substances, e.g., polymeric substances.

By "paste" is meant a soft, viscous mass of solids dispersed in a liquid.

A "particle" means a substance being a solid having a shape which can be geometrically determined. Particles can typically be analysed with respect to e.g. grain size.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

A substance is classified as "liquids" if it has a viscosity below about 100 Pa*s or below about 50 Pa*s or below about 5 Pa*s at 25° C.

A "Newtonian liquid" is a liquid which is characterized as follows: For straight, parallel and uniform flow, the shear stress between layers is proportional to the velocity gradient in the direction perpendicular to the layers. The measured viscosity is often also referred to as "dynamic viscosity" or "Newtonian viscosity". Many fluids, such as water and most gases, satisfy Newton's criterion and are known as Newtonian fluids. Non-Newtonian fluids exhibit a more complicated relationship between shear stress and velocity gradient than simple linearity.

If not otherwise indicated "molecular mass" always means Mw (weight average molecular mass) and can either be taken from the product specification or can be determined by suitable measurement methods known to the person skilled in the art, such as sedimentation velocity.

The term "essentially free of a substance" is to be understood that a certain substance is typically not present at all or has not been willfully added. However, it might happen that sometimes unavoidable traces of this substance can be detected such as water absorbed or adsorbed on the surface of an additive.

A "hardenable matrix" may be described as the components of a composition contributing to the formation of a network due to chemical interaction (e.g. formation of chemical bondings) between the components thereby leading to a significant change in rheological properties like viscosity.

The terms "vulcanizing, hardening, crosslinking, setting" are used interchangeable and refer to silicones that have as a common attribute the development of a crosslinked elastomer from relatively low molecular weight linear or branched polymers by means of a chemical reaction that simultaneously forms these crosslinks and effectively extends chain length at room temperature. "Room temperature vulcanizing" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods.

The term "crosslinked polymer," as used herein, refers to polymers that react with the functional group or groups of the polymer chains to lengthen them and connect them, e.g., to form a crosslinked network characteristic of a silicone elastomer. In contrast to a thermoplastic polymer (i.e., a polymer that softens and flows upon heating) a crosslinked polymer, after crosslinking, is characteristically incapable of further flow.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is carried out by placing a liquid material into the mouth in a customised tray. The material then sets to become an elastic solid, and when removed from the mouth retains the shape of the teeth. Common materials used for dental impressions are sodium alginate, agar, polyethers including aziridino substituted polyether materials and silicones, both condensation-cured silicones and addition-cured silicones including polyvinyl siloxanes.

Surfactants, also sometimes referred to as tensides, are wetting agents that are able to lower the surface tension of a liquid, allowing easier spreading, and lower the interfacial tension between two liquids.

Surfactants are usually organic compounds that are amphiphilic, meaning they contain both hydrophobic groups ("tails") and hydrophilic groups ("heads"). Typical examples include polyethyleneglycol-substituted fatty acids.

Usually, a surfactant can be classified by the presence of formally charged groups in its head. A nonionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitterionic.

Surfactants typically reduce the surface tension of water by adsorbing at the liquid-gas interface. They also may reduce the interfacial tension between oil and water by adsorbing at the liquid-liquid interface. Many surfactants can also assemble in the bulk solution into aggregates. Some of these aggregates are known as micelles. The concentration at which surfactants begin to form micelles is known as the critical micelle concentration (CMC).

Surfactants can also be characterized by a "Hydrophobic Lipophilic Balance" value (HLB-value). Generally, with an increasing HLB-value a substance becomes more hydrophobic and in reverse more lipophilic. The measurement of the HLB-value of a certain substance can be accomplished by determining its aqueous solubility and cloud point, using e.g. the method described by H. Schott, J. Pharm. Science, 58, 1442, (1969). E.g. according to the product description, Silwett L-77 (a Si-containing surfactant) is said to have an estimated HLB value in the range of 5 to 8.

The term "automixer-suitable impression material" relates to a multi-component impression material (e.g. containing a base and catalyst paste) which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™" and "Pentamix™2" devices of 3M ESPE Company (cf. U.S. Pat. No. 5,286,105 and U.S. Pat. No. 5,249,862).

A "dental compositions and dental articles" within the meaning of the present invention is a composition which is to be used in the dental field (including restorative and prosthodontic work) including the orthodontic area. In this respect, a dental composition typically does not contain hazardous substances. Commercially available products have to fulfil certain requirements such as those given in ISO 4823. Typically, those compositions cure or set at ambient conditions.

An "aziridinopolyether" means a material having a backbone comprising polyether moieties (e.g. moieties which can be obtained by polymerising ethylene oxide and/or tetrahydrofuran) and comprising at least two aziridino moieties as reactive side groups. Polymers or prepolmyers containing aziridino moieties typically cure by a cationic polymerisation mechanism.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

A "wax" is defined as a substance or a mixture of substances, naturally or artificially obtained, with at least five of the following properties:
1. at 20° C. kneadable, solid to fragile hard;
2. rough to fine crystalline, transparent to opaque, but not vitreous;
3. above 40° C. melting without decomposition;
4. already little above the melting point relatively low viscous;
5. strong temperature-dependent consistency and solubility;
6. polishable with low pressure

DETAILED DESCRIPTION OF THE INVENTION

The present invention provides dental impression materials having sufficient shear thinning properties.

Surprisingly, they additionally have a better shelf life compared to impression materials known from the art in the uncured state. It was found that the rheological modifiers, i.e. the (modified) amide wax can be formulated together with the reactive component(s) of the dental impression material. Residual water in the inventive impression materials is typically less critical compared to state of the art formulations. Costly processes like drying of the components of the formulation before the formulation step can often be omitted.

Further, the materials containing the (modified) amide wax according to the invention show better shelf life stability of the polymerized or cured materials. During storage, the impressions made of materials of the state of the art with conventional triglycerides as rheology modifiers often develop a smeary surface indicating that the impression cannot be casted with gypsum after a certain time. In contrast to this, impressions made of materials containing the inventive (modified) amide wax typically still show a dry surface under the same storage conditions.

This means that the materials containing (modified) amide wax according to the invention provide the opportunity to provide materials which can be stored for a longer period of time compared to known materials, wherein the cured material still can be casted with gypsum. This means a higher acceptance and more convenience for the dentists and dental laboratories as they have more time for casting the impression made with gypsum in order to obtain a positive model of the dental situation.

Another aspect of the invention is that usually the (modified) amide wax in the materials of the invention can be used in a relatively low amount. Thus, less rheological modifier is required for obtaining the desired properties. This offers the opportunity to add other components like monomer(s), pre-polymer(s) and/or catalyst(s).

The inventive process allows the formulation of the pastes using a single production device and the production in a single step which makes the process more cost efficient.

Especially the formulations with aziridino polyethers of the present invention show a higher shear thinning behaviour compared to the formulations containing e.g. tri-glycerides. Especially the base pastes show very high shear thinning properties. But also the catalyst pastes can be adjusted to very good shear thinning properties.

Moreover, it was found that the improved properties can even be achieved without using rheological modifiers known in the state of the art like fats, waxes and triglycerides and/or highly dispersed silica or oxides.

The dental impression material of the invention comprises at least one amide wax and/or at least one modified amide wax.

A wax from the chemical structure could be, e.g. an ester of a long-chain fatty acid with a long-chain alcohol as well as a long-chain aliphatic acid, alcohol and hydrocarbon. It can also have another chemical structure as long as it shows at least five of the above mentioned wax properties.

A (modified) amide wax according to this invention is a compound and/or a mixture of compounds that fulfil at least five of these above mentioned criteria.

Additionally, the (modified) amide wax according to the present invention is a compound or a mixture of compounds wherein at least one compound of the mixture must contain at least one amide group. The amide group can be characterized by the following formula: $NR_1R_2—(C=O)—$, with R1 and R2 being independently selected from H, C1 to C12 or C2 to C6 alkyl, aryl, alkylaryl, alkenyl, wherein 1 to about 5 C atoms can be replaced by atoms including N, O and S.

The amide wax and/or the modified amide wax may function as a kind of rheological modifier. Thus, the components or the mixture of the components of the polymerizable dental impression material without the wax may form a Newtonian liquid. After adding the (modified) amide wax to this components or mixture thereof, the composition shows shear thinning.

An amide wax as used in this invention includes the reaction products of fatty acids with amines. Preferred are modified amide waxes including compounds that are artificially modified by reaction of different reactants, e.g. polyolefinic compounds. According to another embodiment the amides waxes are blends of different compounds, e.g. a polyolefin modified blend of polyamides. Preferred embodiments include amide waxes and/or modified amide waxes containing primary amide groups of the type of $—(C=O)—NH_2$.

The amide wax and/or the modified amide wax used in the present invention often is a mixture of compounds containing at least one compound that is an amide wax or a modified amide wax according to the above mentioned definition. Thus, the mixture of compounds that form the amide wax and/or the modified amide wax may further contain an ethylenically unsaturated group. This ethylenically unsaturated group may be a part of the amide group bearing compound. Likewise the ethylenically unsaturated group may be a part of another compound of the mixture of compounds that form the amide wax.

Additionally, the amide wax and/or the modified amide wax may be mixtures of compounds containing polymeric products of ethylene, propylene and/or polybutadiene. The melting temperature or the area of melting temperatures of the used amide wax and/or the used modified amide wax is above about 60° C. In certain embodiments of the invention the melting temperature or the area of melting temperatures of the used amide wax and/or the used modified amide wax is above about 80° C. or above about 100° C., or above about 110° C.

There is no particular upper limit for the melting temperature, however, the melting temperature of the wax and/or the used modified amide wax is typically below about 250° C. or below about 200° C.

A useful melting temperature range includes a range from about 60° C. to about 250° C. or about 80° C. to about 200° C.

The amide waxes and/or the modified amide waxes are essentially insoluble in common organic and inorganic solvents. Insoluble means that these compounds do not form a homogeneous solution at ambient conditions with an organic or inorganic solvent (e.g., solvents like water or n-hexane).

The amide waxes and/or the modified amide waxes of the present invention are obtainable by reaction of carbonic acids having 12 to 24 C-atoms, or carbonic acids having 16 to 20 C-atoms or carbonic acids having 18 C-atoms with an amine.

For example, the amide waxes and/or the modified amide waxes are available from a non-aromatic $C_{12}$-$C_{24}$ carbonic acid which is reacted with $NH_3$ and/or a substance containing $NH_3$-equivalents (e.g. $NH_4Cl$, $KNH_2$ or the like) and/or an organic mono-amine (e.g. methylamine or ethylamine) and/or an organic diamine (e.g. 1,2-ethylene diamine or, 1,3-propylene diamine).

Preferred acids are ricinoleic acid, rhicinolic acid and other fatty acids having 18 C-atoms that might be completely or partly hydrogenated.

In one preferred embodiment, the acids used to obtain the amide wax and/or the modified amide wax are 1-mono acids.

All above mentioned carbonic acids might be reacted with different amines. However it can be preferred to react the carbonic acids with $NH_3$ or substances which can be used as $NH_3$ equivalents and/or with organic diamines like 1,2-ethylene diamine.

Preferably, the reaction components that are used to obtain the amide wax and/or the modified amide wax are non-aromatic.

The amide waxes and/or the modified amide waxes may include commercially available compounds and mixtures or combination of compounds. Suitable amide waxes and/or modified amide waxes include for instance waxes sold under the trade name Luvotix AB (Lehmann & Voss, Hamburg), Luvotix EAB (Lehmann & Voss, Hamburg), EX M 1525 (Süd-Chemie, Moosburg), Ceraflour 960 and other Ceraflour-Types (Krahn Chemie, Hamburg).

According to one embodiment, the amide wax and/or the modified amide wax has essentially no basic or acidic functional groups. If the amide wax and/or the modified amide wax is a mixture of compounds this mixture is essentially free of basic or acidic substances. Basic substances which are typically not present are e.g. substances containing alkoxide groups (e.g. $RO^-$). Acidic substances which are typically not present are e.g. substances containing sulfonic acid and/or phosphoric acid groups.

According to one embodiment, the amide wax and/or the modified amide wax has an acid number of below about 5 mg KOH/g or below about 4 mg KOH/g (measurable by titration). The amide number might be below about 25 mg KOH/g or below about 20 mg KOH/g (measurable by titration).

In one embodiment of this invention it can be preferred if the amide wax and/or the modified amide wax does not contain any polymerizable N-alkylaziridine-groups.

According to one embodiment, the particle size of the amide wax and/or the modified amide wax in one embodiment of this invention is about $d_{50}<50$ μm or about $d_{50}<15$ μm. A possible particle size distribution is, for example, $d_{50}<4$ μm, $d_{10}<0.8$ μm and $d_{90}<110$ μm.

A common method for determining the particle size is described in the definition section above.

The term d50/μm with regard to particle size measurement means that in 50% of the analyzed volume, the particles have a size below x μm. E.g., a particle size value of below 100 μm (d50/μm) means that within the analyzed volume, 50% of the particles have a size below 100 μm.

The polymerizable dental impression material can be based on different types of chemistry. E.g. polyether impression materials curing by a cationic ring-opening polymerization of aziridines, polysiloxanes curing via a hydrosilation reaction, polysiloxanes curing via a condensation mechanism, mixtures of polyethers and siloxanes curing via a hydrosilation mechanism or polyethers curing via a condensation mechanism can be used.

Thus, in a further embodiment of the invention the polymerizable dental impression material contain a polyether compound containing N-alkylaziridine-groups, a catalyst compound, a filler, optionally additives selected from the group consisting of dyes, pigments, flavourings, stabilizers, retarders and accelerators, auxiliary compounds and combinations thereof and at least one amide wax and/or at least one modified amide wax as described in the text of the invention.

An example for suitable polyether compounds, including monomers and/or pre-polymers is described e.g. in DE 197 11 514 A1 (also published as U.S. Pat. No. 6,395,801), WO 02/102877 (also published as U.S. Pat. No. 7,276,545) or DE 17 45 810 C (also published as US U.S. Pat. No. 3,453,242) the content and disclosure of which is herewith incorporated by reference.

Suitable initiators for such polymerizable dental impression materials include e.g. oxonium, ammonium and sulfonium salts as well as the initiating systems described in U.S. Pat. No. 4,167,618, DE 10 018 918 (also published as US 2003/0153726), EP 0 279 238 A1 (also published as U.S. Pat. No. 4,867,790), DE 199 42 459 A1 (also published as U.S. Pat. No. 6,894,144) and WO 2007/016295 A1 the content and disclosure of these documents is herewith incorporated by reference.

The inventive dental impression material can optionally contain one or more filler(s). Organic and inorganic fillers which do not cause undesired reactions (e.g. during storage and/or after mixing of separately stored components) in the mixtures of the respective components are preferred.

The fillers are typically solids at ambient conditions and have a $SiO2$ content of more than about 75% by weight. Examples include quartz powder and finely divided silicas of synthetic or natural origin, as inorganic fillers, pyrogenic silicas and precipitated silicas, which can also be used in surface-modified form, and diatomaceous earth from different sources.

As organic fillers waxy substances and fats which are solid at room temperature and temperatures up to about 40° C., like trisacylglycerides, can be used. Trisacyl esters of glycerol of nonanimal origin in combination with inorganic solids are possible as well. Further suitable fats are described in DE 197 11 514 A1 (also published as U.S. Pat. No. 6,127,449), the content and disclosure of which is herewith incorporated by reference.

Other triacyl esters of glycerol may comprise modified fats of vegetable origin, for example of hydrogenated palm oil or soybean oil or of synthetic fats.

The dental impression materials may further contain additives. Additives may be present in an amount from about 0 to about 10% by weight of the total formulation, or from about 0 to about 8% by weight, or from about 0.001 to about 8% by weight, or from about 0.01 to about 8% by weight or from about 0.1 to about 8% by weight.

Typical additives include dyes and pigments, such as iron oxides, (e.g., Sicovit™ yellow iron oxide hydrate), flavourings, retarders, surfactants and mixtures or combinations thereof.

Flavourings which can be added include natural aromas; (e.g. Karthäuser™ grapefruit and mint aromas, spearmint aroma and peppermint oil).

Retarders which can be added include amine or alkaline retardants, for example, soluble imidazole compounds, 1-aryl- and 1-alkyl-substituted imidazoles like those mentioned e.g. in DE 32 45 052 (also published as U.S. Pat. No. 4,532,268).

Surfactants which can be added include nonionic surfactants; silicone polyether surfactants, block copolymers of EO/PO, alkylphenol derivatives, and fatty alcohol derivatives, such as, for example, those mentioned in DE 43 06 997 A1 (also published as U.S. Pat. No. 5,569,691).

The dental compositions according to the invention are typically multi component materials which comprise at least a curable base paste and a catalyst paste comprising a catalyst for curing at least part of the material of the base paste.

Accordingly, the components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base paste and a catalyst paste separated from each other before use, wherein the base paste comprises components the curable material, and the catalyst paste comprises the catalyst suitable for curing the curable material, and wherein the wax and the optional components are present either in the base paste or the catalyst paste or in the base paste and the catalyst paste.

The volume ratios of catalyst paste and base paste can range from about 10:1 to about 1:10. Particularly preferred volume ratios of base paste to catalyst paste are about 1:1 and about 5:1 (5 parts of base paste to 1 part of catalyst paste).

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. No. 5,924,600, U.S. Pat. No. 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as are described e.g. in U.S. Pat. No. 5,249,862, U.S. Oat. No. 5,286,105 and U.S. Pat. No. 5,332,122. The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2.

In practice, the impression material can be syringed through a static or mechanical mixing device into an impression tray or onto patient's teeth or tissue and placed in the patient's mouth. After the impression material is set, the tray is removed from the patient's mouth and, in instances where the dental practitioner prepares the positive model, it may be preferable to pour the positive model material immediately after removal of the impression from the patient's mouth.

A possible process to manufacture the polymerizable dental impression material of the invention typically comprises the steps of:
(a) heating one ore more of the liquid ingredients of a dental impression material to a temperature of about 40 to about 140° C., or about 60 to about 120° C.,
(b) adding at least one amide wax and/or at least one modified amide wax to the heated liquid mixture wherein the amide wax and/or the modified amide wax has a melting temperature or an area of melting temperatures above the temperature to which the ingredients of step (a) are heated,
(c) incorporating the amide wax(es) and/or the modified amide wax(es) to the mixture by dissolving it with a dissolver at a temperature which is below the melting temperature or below the area of melting temperatures of the added amide wax(es) and/or the modified amide wax(es) until the mixture becomes clear,
(d) optionally adding additives,
(e) cooling the mixture down to room temperature (23° C.), and
(f) optionally adding flavourants.

If desired one or more of the described process steps can be carried out under reduced pressure (e.g. below about 100 mbar or below about 50 mbar or below about 10 mbar).

After the amide wax(es) has/have been added and dispersed, further additives can be added at least partially, if desired. Additives are typically added before the mixture undergoes a cooling process. Flavouring, however, are typically added after a cooling step has been conducted.

Working at temperatures above room temperature (e.g. 23° C.) and under reduced pressure can be advantageous for instance to remove residues of humidity and air from the formulation, to better homogeneously incorporate fillers and to reduce process time.

The liquid ingredients of the polymerizable dental impression material show Newtonian behaviour at room temperature. After incorporating the (modified) amide wax they then show a pseudoplastic behaviour and shear thinning.

If the wax has a melting temperature outside the range or below the melting temperature or area of melting temperatures described in the invention, the wax starts melting during the production process and afterwards typically does not function as a rheological modifier. That is, the obtained composition does not show the desired shear-thinning behaviour.

The amide wax and/or the modified amide wax are typically incorporated into the liquid ingredients of a dental impression material. It can be desirable that the amide wax and/or the modified amide wax has a melting temperature or an area of melting temperatures that is above the elected dispergation temperature. A suitable dispergation temperature for the use of the amide wax and/or the modified amide wax in the base paste includes a temperature in the range between about 60 to about 140° C. or between about 60 and about 120° C.

To incorporate the amide wax and/or the modified amide wax to the heated mixture of liquid ingredients of the dental impression material it can be dissolved with a dissolver. This dissolver may contain a butterfly or a cross blade agitator for slow rotating with a rotating speed of about 20 to about 1000 $s^{-1}$ and/or a toothed disk or a double disk for fast rotating with a rotating speed of about 100 to about 2500 $s^{-1}$ or about 1500 to about 2200 $s^{-1}$.

It can be preferred if the liquid ingredients of the dental impression material contain at least one aziridinopolyether. Otherwise, the liquid ingredients of a dental impression material can contain at least one compound capable to dissolve an initiator that initiates the polymerization of an aziridinopolyether.

In another embodiment the liquid ingredients of a dental impression material contain at least one functionalized or unfunctionalized polysiloxane.

The impression material of the invention is typically provided as a kit of parts containing a base part and a catalyst part, wherein the catalyst part contains components needed for starting the hardening process of the hardenable components being present in the base paste. The amide wax and/or the modified amide wax can be added to the base paste or the catalyst paste or the base paste and the catalyst past. According to a preferred embodiment, the amide wax and/or the modified amide wax is added to the base paste only.

The pastes may be delivered to the dentist for instance in tubes, foil bags or plastic cartridges. It can be desirable to ensure a shelf life at room temperature for about 12 months or even a longer period of time. Since the process steps of formulating the pastes and the process parameters applied in the individual process steps may influence the shelf life of the resulting pastes, it might be advantageous to apply different parameters for different pastes. The parameters chosen may depend for instance on the viscosity of the resulting pastes, but also on amount, compatibility or properties like viscosity or stability of the substances used. In particular, it might be advantageous to apply one parameter set for formulating the paste containing the catalyst and another, different parameter set for formulating the base paste.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, all molecular weights are weight average molecular weight and all measurements were done at ambient conditions (23° C.).

EXAMPLES

Test Methods/Measurement

Shore Hardness A:

Shore Hardness A is a very convenient method to obtain data about the degree of vulcanization. The value of Shore Hardness is a common number in dentistry to characterize a cured impression material.

Time dependant measurements were done according to DIN 53505. For determination of the values three independent measurements were performed. A "Handhärteprüfgerät Zwick 3150" (Zwick GmbH & Co, Ulm) was used as the measuring device. The accuracy of the given values is ±1.

Viscosity

The viscosity is a commonly used parameter to characterize the rheological behavior of pasty systems.

For the measurement a rheometer with a plate/plate-system (diameter: 20 mm) was used. During the measurement which was accomplished at 23° C., a constant measuring gap was adjusted at 0.2 mm. A viscosity curve of the paste was provided by variation of the shear rate. During the examination the shear rate was increased from 10 to 100 1/s in steps of 10 1/s. Each measuring point was kept for 5 seconds. Two independent measurements were performed. A "Physica Rheometer MCR300" (Anton Paar GmbH, Graz) was used as the measuring device.

Formulations:

In all formulations the (modified) amide wax according to the invention was formulated into the base pastes. Additionally, a formulation with the inventive (modified) amide wax in the catalyst paste was performed, too.

General Procedure to Formulate Base Pastes with Conventional Tri-Glycerides (Base Paste 1 and 6)

All liquid components and the fat (triglyceride) were mixed in a vessel and warmed up to about 90° C. under agitation. When the fat was melted, the liquid was shock-cooled by using a chill roll. Finally the pigment paste and the filler were added with a kneading machine.

General Procedure to Formulate Base Pastes with (Modified) Amide Waxes (Base Paste 2, 3, 4 and 5):

An eccentrically dissolver (PC-Laborsystem; Magden, Switzerland) was used. All liquid components were added into the vessel. Then they were heated to about 70° C. under agitation. Afterwards, the (modified) amide wax was added and dispersed for about 15 minutes at the same conditions with a wheel peripheral speed of 10 m/s. Subsequently the filler was added into the vessel and dispersed for further 45 minutes at about 70° C. with a wheel peripheral speed of 10 m/s.

The formulation of base paste 7 is based on the formulation of base paste 2 with the exception that an oleic acid mono ethanolamide (Telamide) having a melting point of 52° C. was used instead of the (modified) amide wax.

General Procedure to Formulate Catalyst Paste 1, 2 and 5

Sulfonium salt tetrafluoroborate and the surfactant were solved in acetyl tributyl citrate at 50° C. Afterwards the solution has been cooled down at 23° C. Finally, the diatomaceous earth, the highly dispersed silica and the pigments were kneaded in with a three-finger kneading machine (3M ESPE, Seefeld).

Formulation for Catalyst Paste 3: see Example F in WO 2004/098542

Formulation for Catalyst 4:

P-toluene sulfonic acid was solved in N-ethyl-o,p-toluene-sulfonamide at 23° C.

Formulation for Catalyst Paste 6

Sulfonium salt tetrafluoroborate and the surfactant were dissolved in acetyl tributyl citrate at 50° C. Afterwards the amid wax was added to the mixture and dispersed for 30 minutes at the same conditions with a wheel peripheral speed of 17 m/s. Finally, the diatomaceous earth and the pigments were kneaded in with a butterfly stirrer with a wheel peripheral speed of 3 m/s. To disperse the rheology modifier according to the invention an eccentrically dissolver (PC-Laborsystem; Magden, Switzerland) was used.

Test System 1

Base Paste 1

69.00% difunctional aziridino polyether Mn: 6000 (from EO (ethylene oxide)/THF (tetra hydro furane)

0.65% imidazole compound (according to DE 3245052)

3.00% N-ethyl-o,p-toluolsulfonamide, (Fuji Amide Chemicals Co. Ltd) N-ethyl-o-toluolsulfonamide; CAS 1077-56-1 (60-70%), N-ethyl-p-toluolsulfonamide; CAS 80-39-7 (20-30%)

8.35% dibenzyl-toluene (Atofina, CAS-No 26898-17-9)

5.00% fat (trisacyclic ester of glycerine (Sasol Germany GmbH)

14.00% cristobalit, surface treated (Quarzwerke Frechen, CAS-No 238-455-4)

Catalyst Paste 1

19.3% sulfonium salt tetrafluoroborate (according to U.S. Pat. No. 4,167,618)

40.5% acetyl tributyl citrate (Croda Surfactants Ltd, CAS 77-90-7)

3.5% surfactant (copolymer EO/PO) (C. H. Erbslöh KG, CAS-No 9003-11-6)

12.1% diatomaceous earth (Solvadis Specialities GmbH, CAS-No 68855-54-9)

24.1% highly dispersed silica, surface treated (HDKH™, Wacker, CAS-No 68909-20-6)

0.5% pigments

Test System 2

Base Paste 2

69.00% difunctional aziridino polyether Mn: 6000 (from EO (ethylene oxide)/THF (tetra hydro furane)

0.65% imidazole compound (according to DE 3245052)

3.00% N-ethyl-o,p-toluolsulfonamide, (Fuji Amide Chemicals Co. Ltd) N-ethyl-o-toluolsulfonamide; CAS 1077-56-1 (60-70%), N-ethyl-p-toluolsulfonamide; CAS 80-39-7 (20-30%)

8.35% dibenzyl-toluene (Atofina, CAS-No 26898-17-9)

5.00% blend of different fatty acid amids (Lehmann&Voss, Hamburg, Luvoitx EAB), melting point: approx. 120° C.

14.00% cristobalit, surface treated (Quarzwerke Frechen, CAS-No 238-455-4)

Catalyst Paste 2

19.3% sulfonium salt tetrafluoroborate (according to U.S. Pat. No. 4,167,618)
40.5% acetyl tributyl citrate (Croda Surfactants Ltd, CAS 77-90-7)
3.5% surfactant (copolymer EO/PO) (C. H. Erbslöh KG, CAS-No 9003-11-6)
12.1% diatomaceous earth (Solvadis Specialities GmbH, CAS-No 68855-54-9)
24.1% highly dispersed silica, surface treated (HDKH™, Wacker, CAS-No 68909-20-6)
0.5% pigments Test System 3

Base Paste 3

62.73% difunctional vinyl polydimethylsiloxane PDMS back bone; η=9000-11000 mPas (Wacker-Chemie, Munich, CAS 68083-19-2)
9.09% polydimethylsiloxane, η=100 mPas; SiH: 3.8 mmol/g (Hanse-Chemie, CAS-No 68037-59-29)
4.55% blend of different fat acid amids (Lehmann & Voss, Hamburg, Luvoitx EAB), melting point: approx. 120° C.
12.73% cristobalit, surface treated (Quarzwerke Frechen, CAS-No 238-455-4)
8.18% dibenzyl-toluene (Atofina, CAS-No 26898-17-9)
2.73% N-ethyl-o,p-toluolsulfonamide, (Fuji Amide Chemicals Co. Ltd) N-ethyl-o-toluolsulfonamide; CAS 1077-56-1 (60-70%), N-ethyl-p-toluolsulfonamide; CAS 80-39-7 (20-30%)

Catalyst Paste 3

Example F in WO 2004/098542

Test System 4

Base Paste 4

69.00% Geniosil STP-E15 (Wacker, CAS-No 216597-12-5)
3.00% N-ethyl-o,p-toluolsulfonamide, (Metall-Chemie, CAS-No 1077-66-1, 80-39-7)
9.00% dibenzyl-toluene (Atofina, CAS-No 26898-17-9)
5.00% blend of different fat acid amides and olefinic products (Lehmann & Voss, Hamburg Luvoitx EAB), melting point: approx. 120° C.
14.00% cristobalit, surface treated (Quarzwerke Frechen, CAS-No 238-455-4)

Catalyst 4

2.0% p-toluene sulfonic acid (Merck; CAS-No 6192-52-5)
98.0% N-ethyl-o,p-toluolsulfonamide (Fuji Amide Chemicals Co. Ltd) N-ethyl-o-toluolsulfonamide; CAS 1077-56-1 (60-70%), N-ethyl-p-toluolsulfonamide; CAS 80-39-7 (20-30%)

Test System 5

Base Paste 5

69.00% difunctional aziridino polyether Mn: 6000 (from EO (ethylene oxide)/THF (tetra hydro furane)
0.65% imidazole compound (according to DE 3245052)
3.00% N-ethyl-o,p-toluolsulfonamide, (Fuji Amide Chemicals Co. Ltd) N-ethyl-o-toluolsulfonamide; CAS 1077-56-1 (60-70%), N-ethyl-p-toluolsulfonamide; CAS 80-39-7 (20-30%)
9.00% dibenzyl-toluene (Atofina, CAS-No 26898-17-9)
5.00% Amid wax (Südchemie, Moosburg, EX M 1525), melting point: 135° C.
14.00% cristobalit, surface treated (Quarzwerke Frechen, CAS-No 238-455-4)

Catalyst Paste 5

19.3% sulfonium salt tetrafluoroborate (according to U.S. Pat. No. 4,167,618)
40.5% acetyl tributyl citrate (Croda Surfactants Ltd, CAS-No 77-90-7)
3.5% surfactant (copolymer EO/PO); (C. H. Erbslöh KG, CAS-No 9003-11-6)
12.1% diatomaceous earth (Solvadis Specialities GmbH, CAS-No 68855-54-9)
24.1% highly dispersed silica, surface treated (HDKH™, Wacker, CAS-No 68909-20-6)
0.5% pigments Test System 6

Base Paste 6

53.50% difunctional aziridino polyether Mn: 6000 (from EO (ethylene oxide)/THF (tetra hydro furane)
0.54% imidazole compound (according to DE 3245052)
14.7% non reactive polyether Mn: 6000 (from EO (ethylene oxide)/THF (tetra hydro furane)
8.1% dibenzyl-toluene (Atofina, CAS-No 26898-17-9)
15.1% fat (trisacyclic ester of glycerine (Sasol Germany GmbH)
6.5% diatomaceous earth (Solvadis Specialities GmbH, CAS-No 68855-54-9)
1.6% pigment paste Catalyst Paste 6

19.3% sulfonium salt tetrafluoroborate (according to U.S. Pat. No. 4,167,618)
40.5% acetyl tributyl citrate (Croda Surfactants Ltd, CAS-No 77-90-7)
3.5% surfactant (copolymer EO/PO); (C. H. Erbslöh KG, CAS-No 9003-11-6)
12.1% diatomaceous earth (Solvadis Specialities GmbH, CAS-No 68855-54-9)
10.0% blend of different fat acid amides and olefinic products (Lehmann&Voss, Luvotix EAB), melting point: approx. 120° C.
0.5% pigments Test System 7

Catalyst Paste 7

19.3% sulfonium salt tetrafluoroborate (according to U.S. Pat. No. 4,167,618)
40.5% acetyl tributyl citrate (Croda Surfactants Ltd, CAS 77-90-7)
3.5% surfactant (copolymer EO/PO) (C. H. Erbslöh KG, CAS-No 9003-11-6)
12.1% diatomaceous earth (Solvadis Specialities GmbH, CAS-No 68855-54-9)
24.1% highly dispersed silica, surface treated (HDKH™, Wacker, CAS-No 68909-20-6)
0.5% pigments Base Paste 7

69.00% difunctional aziridino polyether Mn: 6000 (from EO (ethylene oxide)/THF (tetra hydro furane)
0.65% imidazole compound (according to DE 3245052)
3.00% N-ethyl-o,p-toluolsulfonamide, (Fuji Amide Chemicals Co. Ltd) N-ethyl-o-toluolsulfonamide; CAS 1077-56-1 (60-70%), N-ethyl-p-toluolsulfonamide; CAS 80-39-7 (20-30%)
8.35% dibenzyl-toluene (Atofina, CAS-No 26898-17-9)
5.00% Telamide (Oleic acid mono ethanolamide, $C_{20}H_{39}NO_2$ Bärlocher; $C_{20}H_{39}NO_2$); melting point: 52° C.
14.00% cristobalit, surface treated (Quarzwerke Frechen, CAS-No 238-455-4)

Measurements
Viscosity
The viscosity of the base paste was measured.

TABLE 1

| Base Paste | Viscosity | | | | | | | | | | | |
|---|---|---|---|---|---|---|---|---|---|---|---|---|
| | 10 1/s | 20 1/s | 30 1/s | 40 1/s | 50 1/s | 60 1/s | 70 1/s | 80 1/s | 90 1/s | 100 1/s | Δ 1/s | [%] |
| 1 | 68 | 60.7 | 56.4 | 53.6 | 51.5 | 50.0 | 48.7 | 47.6 | 46.7 | 45.8 | 22.2 | 32 |
| 2 | 177 | 120 | 102 | 91.2 | 83.9 | 78.4 | 74.0 | 70.5 | 67.4 | 63.7 | 113.3 | 64 |
| 3 | 81 | 59.4 | 49.2 | 42.5 | 37.8 | 33.9 | 30.7 | 27.9 | 25.7 | 22.7 | 58.3 | 72 |
| 4 | 102 | 71.4 | 58.8 | 51.7 | 47 | 43.7 | 41.1 | 39.1 | 37.5 | 35.5 | 66.5 | 65 |
| 5 | 94.2 | 74.7 | 66.9 | 62.5 | 59.5 | 57.3 | 55.5 | 54 | 52.7 | 51.2 | 43 | 45 |
| 6 | n.m | n.m | n.m | n.m | n.m | n.m | n.m | n.m | n.m | n.m | n.m | n.m |
| 7 | 39.7 | 38.3 | 37.2 | 36.4 | 35.7 | 35.2 | 34.8 | 34.4 | 34.1 | 33.7 | 6.0 | 15 | n.m: not measured

The viscosity measured for base paste No. 7 does not change significantly with increasing shear rate indicating that this paste does not show the desired shear thinning properties.
The viscosity of the catalyst paste was measured.

TABLE 2

| Catalyst Paste | Viscosity | | | | | | | | | | | |
|---|---|---|---|---|---|---|---|---|---|---|---|---|
| | 10 1/s | 20 1/s | 30 1/s | 40 1/s | 50 1/s | 60 1/s | 70 1/s | 80 1/s | 90 1/s | 100 1/s | Δ 1/s | [%] |
| 1 | 288 | 178 | 131 | 104 | 87.4 | 76.4 | 68.4 | 61.9 | 56.2 | 53.2 | 234.8 | 81 |
| 6 | 187 | 83 | 53.8 | 39.9 | 33.6 | 28.5 | 25.1 | 22.1 | 19.9 | 18.8 | 168.2 | 90 |

Shore Hardness A

The base paste was reacted with the corresponding catalyst paste at 23° C. for each of the test systems by hand spatulation.

TABLE 3

| Test System | Ratio Base Paste to Catalyst | Shore hardness A after | | | | |
|---|---|---|---|---|---|---|
| | | 8 min | 10 min | 15 min | 30 min | 24 h |
| 1 | 80.6%:19.4% | 46 | 48 | 50 | 51 | 52 |
| 2 | 80.6%:19.4% | 43 | 46 | 50 | 51 | 52 |
| 3 | 50.0%:50.0% | 29 | 29 | 29 | 30 | 31 |
| 4 | 83.3%:16.7% | 12 | 18 | 25 | 30 | 34 |
| 5 | 80.6%:19.4% | 46 | 48 | 49 | 51 | 51 |
| 6 | 80.6%:19.4% | 32 | 35 | 39 | 42 | 43 |
| 7 | 80.6%:19.4% | 32 | 36 | 41 | 44 | 46 |

Using the (modified) amide wax according to the invention lead to a decrease in viscosity at increasing shear rates. This indicates improved shear thinning behaviour of the material.

The paste containing the oleic acid monoethanolamide (Telamide), which was also used in Comparative Example 4 of U.S. Pat. No. 5,569,691, did not lead to a significant decrease in viscosity at increased shear rate.

Further, the materials containing the (modified) amide wax according to the invention showed better shelf life stability of the polymerized materials. After storage for about 4 to about 8 weeks at 23° C., 50% humidity and under ambient daylight exposure, the impressions made of materials with conventional triglycerides as rheology modifiers developed a smeary surface indicating that the impression is not to be casted (e.g. with gypsum) after this time. Contrary, the impressions made of materials with inventive rheology modifiers showed under the same storage conditions after 4-8 weeks still a dry surface. This means that the materials containing rheology modifiers according to the invention even after 4-8 weeks storage were appropriate to be casted with plaster.

The (modified) amide wax can be used in curable dental impression materials together in the same paste with reactive groups like:

Ethylene imine derivatives
Si—H containing substances
$Si(OR)_x$ (R=alkyl preferably methyl, ethyl; x=1, 2, 3) containing substances to improve rheological behaviour of the uncured pastes and to optimize the production process.

Especially formulations with aziridinopolyethers show higher pseudoplaciticity with the rhelogical modifiers than with the tri-glycerides. The inventive formulations are preferably provided as a two paste formulation (kit of parts) in which the rheological additives are formulated together with aziridinopolyethers in the same paste.

In addition the same rheological modifiers can be used in the base paste as well as in the catalyst paste.

The invention claimed is:
1. A polymerizable dental impression material containing
(a) a polyether compound containing N-alkylaziridine-groups,
(b) a catalyst compound,
(c) a filler,
(d) optionally additives selected from the group consisting of dyes, pigments, flavourings, stabilizers, retarders, accelerators, auxiliary compounds, and combinations thereof, and
(e) at least one amide wax and/or at least one modified amide wax wherein the amide wax and/or the modified amide wax is a compound or a mixture of compounds having wax properties and the compound or at least one compound of the mixture has a primary amide group of the type —(C=O)—$NH_2$ and wherein the amide wax and/or the modified amide wax has a melting temperature or an area of melting temperatures of above about 100° C.
2. The polymerizable dental impression material according to claim 1, wherein the amide wax and/or the modified amide wax has essentially no basic or acidic functional groups or is essentially free of basic or acidic substances.

3. The polymerizable dental impression material according to claim 1, wherein the amide wax and/or the modified amide wax is available from a non-aromatic C12-C24 carbonic acid that is reacted with NH3 and/or a substance containing NH3-equivalents and/or an organic mono-amine and/or an organic diamine.

4. The polymerizable dental impression material according to claim 1, wherein the amide wax and/or the modified amide wax further comprises an ethylenically unsaturated group.

5. The polymerizable dental impression material according to claim 1, wherein the amide wax and/or the modified amide wax has a mean particle size of about $d_{50}$<50 µm.

6. The polymerizable dental impression material according to claim 1, wherein the amide wax and/or the modified amide wax is essentially insoluble in water and n-hexane.

7. The polymerizable dental impression material according to claim 1, wherein the amide wax and/or the modified amide wax does not contain any polymerizable N-alkylaziridine-groups.

8. The polymerizable dental impression material according to claim 1, wherein the amide wax and/or the modified amide wax is a rheological modifier.

9. A process of producing a polymerizable dental impression material, comprising the steps of:
  a) heating one or more of the liquid ingredients of a dental impression material to a temperature of about 40 to about 140° C.,
  b) adding at least one amide wax and/or at least one modified amide wax to the heated liquid mixture wherein the amide wax and/or the modified amide wax contains a primary amide group of the type —(C=O)—NH$_2$ and wherein the amide wax and/or the modified amide wax has a melting temperature or an area of melting temperatures above the greater of:
    (i) about 100° C., or
    (ii) the temperature to which the ingredients of step (a) are heated,
  c) incorporating the amide wax(es) and/or the modified amide wax(es) to the mixture by dissolving it with a dissolver at a temperature which is below the melting temperature or below the area of melting temperatures of the added amide wax(es) and/or the modified amide wax(es) until the mixture becomes clear,
  d) cooling the mixture down at room temperature
wherein the polymerizable dental impression material contains
  (a) a polyether compound containing N-alkylaziridine-groups,
  (b) a catalyst compound,
  (c) a filler,
  (d) optionally additives selected from the group consisting of dyes, pigments, flavourings, stabilizers, retarders, accelerators, auxiliary compounds, and combinations thereof.

10. Process according to claim 9, wherein the liquid ingredients of the dental impression material are Newtonian liquids at room temperature.

11. Process according to claim 9, wherein the liquid ingredients of the dental impression material contain at least one compound capable to dissolve the catalyst compound that initiates the polymerization of the polyether compound containing N-alkylaziridine-groups.

12. The polymerizable dental impression material according to claim 1, wherein the amide wax and/or the modified amide wax has a mean particle size of about $d_{50}$<15 µm.

* * * * *

UNITED STATES PATENT AND TRADEMARK OFFICE
CERTIFICATE OF CORRECTION

PATENT NO. : 8,487,016 B2
APPLICATION NO. : 12/809187
DATED : July 16, 2013
INVENTOR(S) : Sebastian Zeller et al.

It is certified that error appears in the above-identified patent and that said Letters Patent is hereby corrected as shown below:

On the Title Page, in Column 2, under (Other Publications)
Line 4, delete "Technal" and insert -- Technical --, therefor.

In the Specification
Column 1
Lines 30-31, delete "Xantropren™," and insert -- Xantopren™, --, therefor.

Column 2
Line 21, delete "alkoxysilylfunctionalized" and insert -- alkoxysilyl functionalized --, therefor.
Line 49, delete "cheep." and insert -- cheap. --, therefor.

Column 3
Line 55, delete "ore" and insert -- or --, therefor.

Column 6
Line 9, delete "fulfil" and insert -- fulfill --, therefor.
Line 17, delete "prepolmyers" and insert -- prepolymers --, therefor.

Column 7
Line 64, delete "fulfil" and insert -- fulfill --, therefor.

Column 9
Line 1, delete "rhicinolic" and insert -- ricinolic --, therefor.

Column 10
Line 32, delete "trisacylglycerides," and insert -- triacylglycerides, --, therefor.

Column 10
Line 32, delete "Trisacyl" and insert -- Triacyl --, therefor.

Signed and Sealed this
Twenty-second Day of October, 2013

Teresa Stanek Rea
*Deputy Director of the United States Patent and Trademark Office*

CERTIFICATE OF CORRECTION (continued)
U.S. Pat. No. 8,487,016 B2

Column 11
Line 53, delete "ore" and insert -- or --, therefor.

Column 14
Line 40, delete "(trisacyclic" and insert -- (tricyclic --, therefor.
Line 66, delete "amids" and insert -- amides --, therefor.
Line 67, delete "Luvoitx" and insert -- Luvotix --, therefor.

Column 15
Line 23, delete "amids" and insert -- amides --, therefor.
Line 24, delete "Luvoitx" and insert -- Luvotix --, therefor.
Line 41, delete "Luvoitx" and insert -- Luvotix --, therefor.

Column 16
Line 19, delete "(trisacyclic" and insert -- (tricyclic --, therefor.

Column 18
Line 39, delete "pseudoplaciticity" and insert -- pseudoplasticity --, therefor.
Line 39, delete "rhelogical" and insert -- rheological --, therefor.